United States Patent [19]

Finkenzeller et al.

[11] 4,171,483
[45] Oct. 16, 1979

[54] DEVICE FOR X-RAY DIAGNOSIS, INCLUDING EDGE SHADOW-FREE COMPRESSION DEVICE

[75] Inventors: Johann Finkenzeller, Tennenlohe; Jakob Derfuss, Dornitz, both of Fed. Rep. of Germany

[73] Assignee: Siemens AG, Munich, Fed. Rep. of Germany

[21] Appl. No.: 329,322

[22] Filed: Feb. 5, 1973

Related U.S. Application Data

[63] Continuation-in-part of Ser. No. 60,275, Aug. 3, 1970, abandoned.

[30] Foreign Application Priority Data

Sep. 21, 1969 [DE] Fed. Rep. of Germany ....... 1942491

[51] Int. Cl.$^2$ ............................................. G03B 41/16
[52] U.S. Cl. .................................. 250/321; 250/482; 250/468
[58] Field of Search .............. 250/321, 313, 526, 469, 250/468, 475, 482

[56] References Cited

U.S. PATENT DOCUMENTS

| | | | |
|---|---|---|---|
| 2,619,599 | 11/1952 | Smith | 250/526 |
| 3,214,586 | 10/1965 | Graham | 250/321 |
| 3,535,518 | 10/1970 | Fischer | 250/469 |
| 3,673,407 | 6/1972 | Wiswell | 250/321 |

FOREIGN PATENT DOCUMENTS 1942491 3/1971 Fed. Rep. of Germany

*Primary Examiner*—Bruce C. Anderson
*Attorney, Agent, or Firm*—Allison C. Collard; Thomas M. Galgano

[57] ABSTRACT

A device for X-ray diagnosis, includes an X-ray tube, an image layer carrier, and a compression device for compressing a portion of the patient to be examined fixed to a side of the image layer carrier directed toward the tube. The compression device has two flat, superimposed, interconnected layers of low X-ray absorption material extending over the entire illuminable surface of the image layer carrier, so that the borders of the layers are not X-rayed. One of the layers is directed toward the tube and is fabricated from an elastically extensible material and the layers define therebetween an inflatable central circular section and a narrow tube-like lead section extending from an edge of the two layers to the central circular section. The compression device permits the patient to be X-rayed in the area of the inflatable circular section and in the area laterally adjacent to the inflatable circular section without producing edge shadows. The device further includes a regulatable device coupled to the lead section for inflating and deflating the central circular section.

3 Claims, 4 Drawing Figures

DEVICE FOR X-RAY DIAGNOSIS, INCLUDING EDGE SHADOW-FREE COMPRESSION DEVICE

The present application is a continuation-in-part of our copending patent application Ser. No. 60,275, filed Aug. 3, 1970 abandoned.

This invention relates to a device for X-ray diagnosis and refers more particularly to an X-ray diagnosis device having a compression device with an inflatable tube-like hollow space and located in the cone of primary rays, preferably upon the side of the image layer carrier which is directed toward the X-ray tube.

A device for X-ray diagnosis which is known in the art has a rigid compression tube with an inflatable covering consisting of rubber. The drawback of this device is that the compression tube due to its thickness is in the way when the device is started and in all investigations which do not require the compression tube. For these reasons and also because the compression tube is fixed to a plate impermeable to rays, it is necessary to remove it out of the ray cone after every use. Furthermore, to provide small compression pressures it is always necessary to maintain the patient at a large distance from the image layer surface which is undesirable as far as clearness of image is concerned.

Another known device consists of a manually operable inflatable compression tube which can be held by a stick and which contains an inflatable rubber ball built into a cylindrical casing. A long use of this compression tube is very tiring for the doctor. Furthermore, the stick and the edge of the casing of the tube provide shadows in locations which are close to the object being examined.

An object of the present invention is the provision of a device for X-ray diagnosis having a compression tube which provides less trouble during use.

Other objects of the present invention will become apparent in the course of the following specification.

In the accomplishment of the objectives of the present invention it was found desirable to provide a compression device consisting of two flat superposed layers of small X-ray absorption, these layers being flat and gastightly interconnected with the exception of a space capable of being blown up and a lead. The lead is connected to a regulatable device.

This construction has the advantage that the compression tube when it is not inflated will not in any way disturb or interfer with the patient due to its completely flat surface, either when starting the X-ray device or during the examination. Furthermore, the doctor is provided with a greater compression range by the compression tube which can be inflated from a flat surface to its full size.

According to a further improvement of the present invention the two layers can extend over the entire illuminated surface of the image layer carrier to avoid edge shadows. Edge shadows of a compression tube could be confused with edge shadows of the organs of a patient. In any event, they complicate lines and shadows upon the X-ray picture. For example, the compression tube of U.S. Pat. No. 2,619,599 produces at the same time several round edge shadows by inner and outer borders of two plates. The manner in which edge shadows are eliminated by the present invention is described in detail hereinafter. Thus it is possible not only to examine the parts of the patient in the neighborhood of the tube but also to mount the compression tube firmly upon the side of the image layer carrier directed toward the X-ray tube and to eliminate all mechanisms for moving the compression tube, since there are no more obstruction reasons for not keeping the compression tube in the ray cone, also as far as the size of the investigating area is concerned.

According to a preferred embodiment of the invention the layer directed away from the X-ray tube can be made of a rigid material. This has the particular advantage that the patient can directly engage the image layer carrier for all compression pressures, which is advantageous as far as the sharpness of image is concerned.

The invention will appear more clearly from the following detailed description when taken in connection with the accompanying drawing showing by way of example only, a preferred embodiment of the inventive idea.

Figure 1:
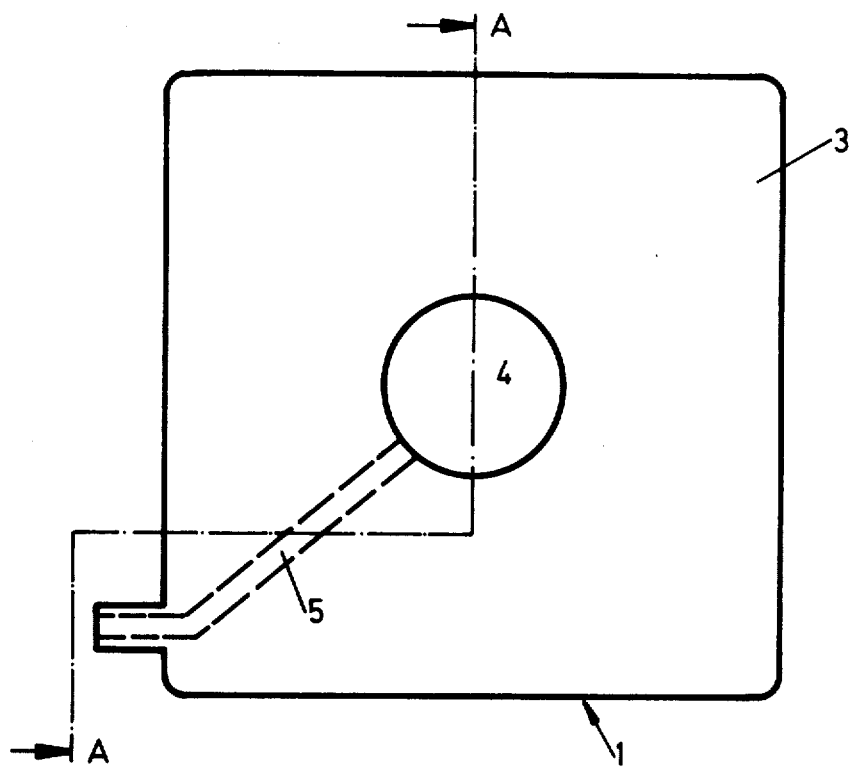
FIG. 1 is a front view of a compression tube of the present invention.
Figure 2:
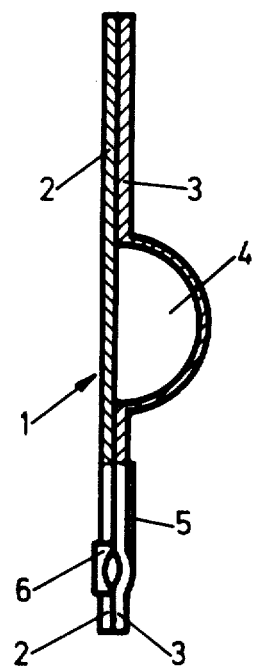
FIG. 2 is a section along the lines A—A of FIG. 1.

FIGS. 1 and 2 show a compression tube device 1 having a flat rigid layer 2 of hard paper. A uniformly thick layer 3 of rubber is gastightly vulcanized upon the layer 2. There are sections, however, wherein the layer 3 is not attached to the layer 2, which form the actual tube-like inflatable hollow space 4 and a space for a lead 5 extending to the space 4. A rubber flap 6 is vulcanized to the hard paper layer 2 at the inlet of the lead and the outer edge of the device 1, the flap 6 being glued with the rubber layer 3 to form an elastic hose prop.

When compressed air is supplied through a hose into this inlet, air will flow through the lead 5 into the space 4, elastically extending the rubber layer 3 and inflating tube-like the portion enclosing the space 4. When compressed air is allowed to escape, the rubber layer will return to its original shape due to its elasticity.

As far as illumination of shadows is concerned, it should be noted that when the inflatable compression cone is not inflated it consists of two flat layers 2 and 3. These layers obviously produce edge shadows at their rectangular edge, namely, where in FIG. 1 the arrow 1 touches the compression cone. However, since the compression cone extends over the entire illuminable surface or X-rayed surface of the image layer, the rectangular edge is outside of the X-rays and cannot be reproduced. The inflatable round section 4 of the layer 3 of the compression cone will not produce any edge shadows when it is not inflated, since it lies flat upon the layer 2 and has no edge. The weakening of the X-rays produced by this layer is constant over the entire illuminable surface, and thus is not visible. When this portion 4 of the layer 3 is inflated, it will rise slowly away from the layer 2 initially without an edge which could be shown. Only in the fully inflated condition shown in FIG. 2, an edge is formed which, due to extension of rubber and resulting diminution of its thickness, will not be reproduced by X-rays. The X-rays will move through the same path in the rubber. Thus, the section 4 is invisible upon X-ray pictures.

It should be noted that each border or edge of each body subjected to X-rays and absorbing them will produce a line on the film. If the body is so large that its edges are outside the film or outside X-rays, its edges will not be seen upon the film. Since the layers 2 and 3 extend over the entire illuminable surface of the image layer carrier, their edges are outside of the X-rays, and therefore will not be represented. Consequently, the entire inflatable section 4 of the rubber layer will not produce any edge shadows.

Figure 4:
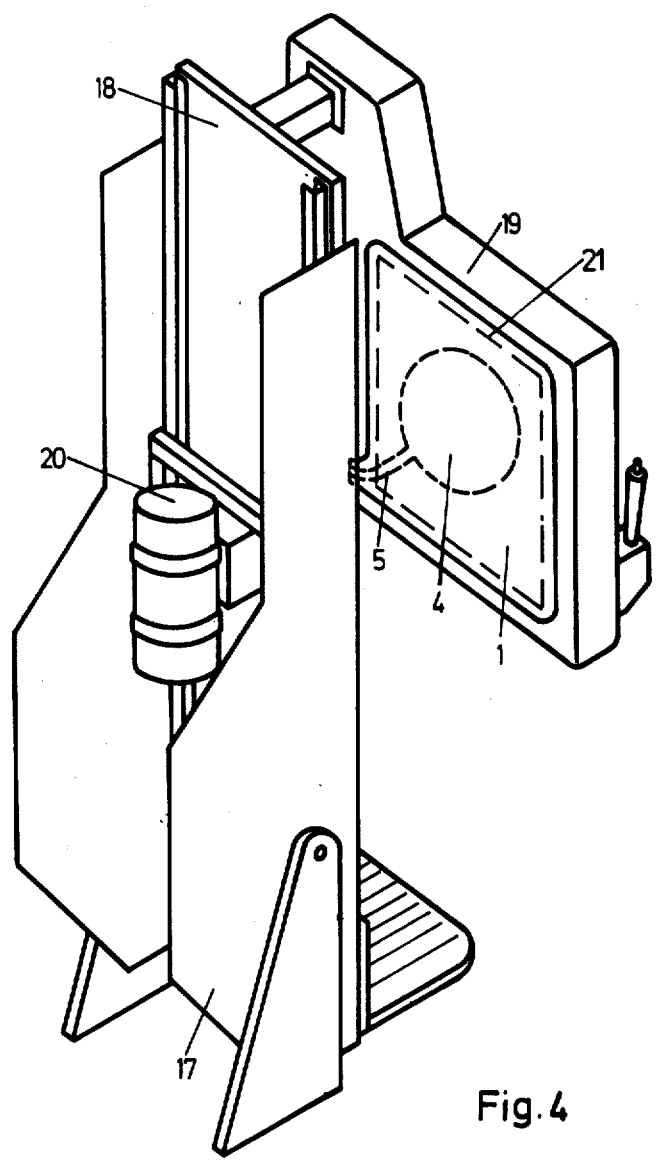
FIG. 4 is a perspective view of an X-ray examining device with a built-in compression tube.

This provides a simple construction free of shadows for the actual inflatable hollow space and for the lead of the tube. FIG. 4 shows an X-ray examining device 17 having a swingable patient supporting plate 18, an image layer carrier 19 constructed as a spotfilm device and located in front of the patient supporting plate and an X-ray tube 20 located behind the patient supporting plate. The image carrier and the X-ray tube are coupled with each other and can be shifted jointly longitudinally and transversely to the patient supporting plate 18. A compression tube 1 is fixed upon the side of the image carrier 19 directed towards the patient supporting plate 18. To avoid formation of edge shades the compression tube extends over the entire surface 21 of the image carrier 19 illuminated by the X-ray tube 20.

The present invention is not concerned with the percentage of the primary X-ray beam absorbed by the rubber layers, since this percentage depends on the hardness of X-rays and the thickness of layers 2 and 3.

Figure 3:
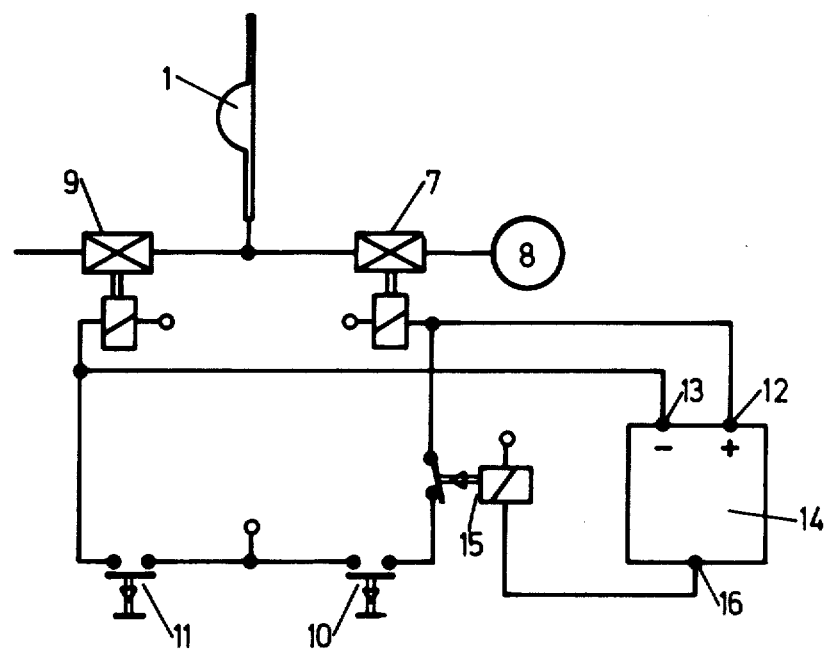
FIG. 3 is a diagrammatic illustration of the circuit supplying compressed air to the compression tube.

The diagram of FIG. 3 shows an inflatable compression tube 1 as being connected for air supply with a source 8 of compressed air through a magnetic valve 7 and as being connected for air removal with outside air through a magnetic valve 9. The magnetic valve 7 used for air supply is connected with a key switch 10 while the magnetic valve 9 used for air removal is connected with a key switch 11. A time integrating device 14 has an addition inlet 12 connected parallel to the magnetic valve 7 and a substraction inlet 13 connected parallel to the magnetic valve 9. The time-integrating device 14 can be of any type well known in the art. A relay 15 has contacts which are closed in position of rest and which are connected to the electrical wiring of the magnetic valve 7 for air supply. The wiring of the relay 15 is connected to the outlet 16 of the time integrating device 14.

When the key switch 10 is actuated, the magnetic valve 7 for air supply will be energized and will open. The compression tube 1 will be inflated until either the switch 10 is released or until a predetermined time has been summed up in the time integrating device 14 through the addition inlet 12 connected parallel to the magnetic valve 7. In that case the time integrating device will energize the relay 15, so that the relay will be actuated and will switch off current to the magnetic valve 7 and to the addition inlet 12 of the device 14. The key switch 11 can be actuated to energize the magnetic valve 9 and permit compressed air to flow out of the compression tube 1. At the same time the duration of air removal is deducted from the time summed up during the inflating phase through the substraction inlet 13 of the time integrating device 14. Due to this arrangement excessive inflating of the compression tube 1 can be avoided, even if it was previously only partially emptied.

An excessive inflating of the compression tube can be also avoided by adapting the maximum inflation pressure to the strength of the rubber layer of the compression tube by means of a reduction valve located between the source of compressed air and the compression tube. Furthermore a spring-actuated switch can be connected with the rear wall of the sighting device or with the hard paper layer of the compression tube to prevent the inflating of the compression tube while the compression tube is not placed against the patient.

What is claimed is:

1. A device for X-ray diagnosis, comprising:
   an X-ray tube;
   an image layer carrier;
   a compression device for compressing a portion of the patient to be examined fixed to a side of the image layer carrier directed toward said tube, said compression device comprising exclusively two flat, superimposed, interconnected layers of low X-ray absorption material extending over the entire illuminable surface of said image layer carrier, so that the borders of the layers are not X-rayed, one of said layers being directed toward said tube and being fabricated from an elastically extensible material, said layers defining therebetween an inflatable central circular section, and a narrow tube-like lead section extending from an edge of the two layers to said central circular section, said compression device in the area of said inflatable circular section and in the area laterally adjacent to said inflatable circular section being non-enclosed to permit the patient to be X-rayed without producing edge shadows; and
   a regulatable device coupled to said lead section for inflating and deflating said central circular section.

2. The device according to claim 1, wherein said regulatable device comprises an electrically operated valve for supplying compressed air to said tube-like section and for inflating said circular section, an electrically operated valve for removing compressed air from said circular section to effect deflation thereof, switching off means connected with the first-mentioned valve and actuating means actuating said switching off means when a pre-determined inflation volume has been reached, said actuation means comprising a time integrating device which adds the time periods when the first-mentioned valve was open, subtracts the time periods when the second-mentioned valve was open and interrupts air supply at a predetermined total time period.

3. The device according to claim 1, wherein said layers are interconnected together by vulcanization.

* * * * *